US012485029B2

(12) United States Patent
Xia et al.

(10) Patent No.: US 12,485,029 B2
(45) Date of Patent: Dec. 2, 2025

(54) BALLOON STENT INSTALLATION DEVICE AND STENT INSTALLATION METHOD

(71) Applicant: SUZHOU ZENITH VASCULAR SCITECH LIMITED, SIP Suzhou (CN)

(72) Inventors: Jie Xia, SIP Suzhou (CN); Liyou Guo, SIP Suzhou (CN)

(73) Assignee: SUZHOU ZENITH VASCULAR SCITECH LIMITED, SIP Suzhou (CN)

( * ) Notice: Subject to any disclaimer, the term of this patent is extended or adjusted under 35 U.S.C. 154(b) by 37 days.

(21) Appl. No.: 18/286,392

(22) PCT Filed: Jun. 8, 2022

(86) PCT No.: PCT/CN2022/097655
§ 371 (c)(1),
(2) Date: Oct. 11, 2023

(87) PCT Pub. No.: WO2023/024645
PCT Pub. Date: Mar. 2, 2023

(65) Prior Publication Data
US 2024/0180729 A1 Jun. 6, 2024

(30) Foreign Application Priority Data
Aug. 27, 2021 (CN) ......................... 202110992776.6

(51) Int. Cl.
*A61F 2/966* (2013.01)
*A61M 25/09* (2006.01)
*A61M 25/10* (2013.01)

(52) U.S. Cl.
CPC .......... *A61F 2/966* (2013.01); *A61M 25/104* (2013.01); *A61M 25/09* (2013.01)

(58) Field of Classification Search
CPC ....... A61F 2/966; A61F 2/958; A61M 25/104; A61M 25/09
See application file for complete search history.

(56) References Cited

U.S. PATENT DOCUMENTS 5,639,274 A 6/1997 Fischell et al.
6,264,671 B1 * 7/2001 Stack ...................... A61F 2/966 606/198

(Continued)

FOREIGN PATENT DOCUMENTS

CN 2783951 Y 5/2006
CN 101267781 A 9/2008

(Continued)

OTHER PUBLICATIONS

International Search Report with English Translation and Written Opinion for PCT Application No. PCT/CN2022/097655, dated Aug. 30, 2022, 12 pages.

(Continued)

*Primary Examiner* — Andrew Restaino
(74) *Attorney, Agent, or Firm* — Dickinson Wright PLLC

(57) ABSTRACT

Provided are a balloon stent installation device and a stent installation method. The balloon stent installation device, which is used to install a self-expandable stent to a lesion site of a blood vessel, includes a balloon dilatation catheter and a stent release tube. The balloon dilatation catheter includes a first through hole with an inlet and an outlet. An expansion part is disposed at a distal end of the balloon dilatation catheter. The self-expandable stent is slidably mounted in the first through hole and located at a distal end of the balloon dilatation catheter. The stent release tube is slidably disposed in the first through hole. A distal end of the stent release tube abuts against the self-expandable stent and includes a second through hole. A micro guidewire is (Continued)

configured to be inserted sequentially through the outlet of the first through hole, the self-expandable stent, and the second through hole.

7 Claims, 5 Drawing Sheets

(56) References Cited

U.S. PATENT DOCUMENTS

| | | | | |
|---|---|---|---|---|
| 2003/0208222 | A1* | 11/2003 | Zadno-Azizi | A61B 17/12045 606/200 |
| 2007/0293931 | A1* | 12/2007 | Parker | A61F 2/958 623/1.11 |
| 2008/0188804 | A1 | 8/2008 | Jordan et al. | |
| 2008/0269868 | A1 | 10/2008 | Bei et al. | |
| 2015/0045871 | A1* | 2/2015 | Beckham | A61F 2/966 623/1.11 |
| 2021/0093349 | A1* | 4/2021 | Nishio | A61B 17/320758 |
| 2021/0401597 | A1* | 12/2021 | Keating | A61F 2/82 |

FOREIGN PATENT DOCUMENTS

| | | | | |
|---|---|---|---|---|
| CN | 102813995 | A | | 12/2012 |
| CN | 103479453 | A | | 1/2014 |
| CN | 102813995 | B | * | 3/2014 |
| CN | 209216785 | U | | 8/2019 |
| CN | 210844903 | U | | 6/2020 |
| CN | 113599037 | A | | 11/2021 |
| CN | 113616397 | A | | 11/2021 |
| CN | 215778936 | U | | 2/2022 |
| EP | 0699451 | A2 | | 3/1996 |
| WO | 2017142579 | A1 | | 8/2017 |

OTHER PUBLICATIONS

First Office Action with English Translation for Chinese Application No. 202110992776.6, dated Jun. 1, 2024, 14 pages.

* cited by examiner

BALLOON STENT INSTALLATION DEVICE AND STENT INSTALLATION METHOD

CROSS-REFERENCES TO RELATED APPLICATIONS

This application is a national stage application filed under 35 U.S.C. 371 based on International Patent Application No. PCT/CN2022/097655, filed on Jun. 8, 2022, which claims priority to Chinese Patent Application No. 202110992776.6 filed with the China National Intellectual Property Administration (CNIPA) on Aug. 27, 2021, the disclosures of which isare incorporated herein by reference in their entireties.

TECHNICAL FIELD

The present application relates to the technical field of stent delivery by balloon dilatation catheters, for example, a balloon stent installation device and a stent installation method.

BACKGROUND

Vascular stenosis, a common vascular disease, is an important cause and risk factor for ischemic vascular disease. Vascular stent implantation is one of the important techniques to treat vascular stenosis.

During the operation of a related vascular stent implantation, a surgeon needs to first deliver a microcatheter and a microguidewire to the lesion, then remove the microcatheter, insert a balloon catheter to pre-expand the lesion, then withdraw the balloon catheter, insert the microcatheter, and then, deliver the stent to the lesion through the microcatheter to release the stent and the stent is automatically stretched to dilate the blood vessel. In the preceding process, the microcatheter and the balloon catheter need to be alternately inserted into the blood vessel multiple times, which is prone to cause complications and increase operation time.

SUMMARY

Embodiments of the present application provide a balloon stent installation device and a stent installation method. With a balloon dilatation catheter installed only once, a self-expandable stent can be delivered and installed, so that a blood vessel can be dilated, operation steps can be reduced, the times of instruments exchanged in a patient's body and operation time can be reduced, and the success rate of the operation can be improved.

In an aspect, a balloon stent installation device is provided, which is configured to install a self-expandable stent to a lesion site of a blood vessel. The balloon stent installation device includes a balloon dilatation catheter and a stent release tube.

The balloon dilatation catheter is provided with a first through hole along the length direction. An inlet is disposed at a proximal end of the first through hole. An outlet is disposed at a distal end of the first through hole. An expansion part is disposed at a distal end of the balloon dilatation catheter. The self-expandable stent is slidably installed in the first through hole. The self-expandable stent is located at the distal end of the balloon dilatation catheter.

The stent release tube penetrates the first through hole through the inlet and is slidably disposed in the first through hole of the balloon dilatation catheter. A distal end of the stent release tube abuts against the self-expandable stent.

The stent release tube is provided with a second through hole along the length direction. The balloon dilatation catheter and the stent release tube are configured such that a micro guidewire can be inserted sequentially through the outlet of the first through hole, the self-expandable stent, and the second through hole.

In another aspect, a stent installation method is provided, which uses the balloon stent installation device described in any of the preceding schemes. The method includes the steps described below.

A compressed self-expandable stent is installed to a distal end of a balloon dilatation catheter, and a stent release tube is installed in a first through hole.

A micro guidewire is inserted sequentially through an outlet of the first through hole, the self-expandable stent, and a second through hole. The balloon dilatation catheter cooperates with the micro guidewire to push an expansion part of the balloon dilatation catheter to a lesion site.

The expansion part expands to stretch out the lesion site.

The expansion part contracts, and the balloon dilatation catheter is withdrawn until the stent release tube pushes the self-expandable stent out of the first through hole.

The balloon dilatation catheter and the stent release tube are withdrawn simultaneously.

BRIEF DESCRIPTION OF DRAWINGS

Drawings used in the description of embodiments of the present application are briefly described below.

REFERENCE NUMBERS OF THE DRAWINGS ARE LISTED AS FOLLOWS

Figure 1:
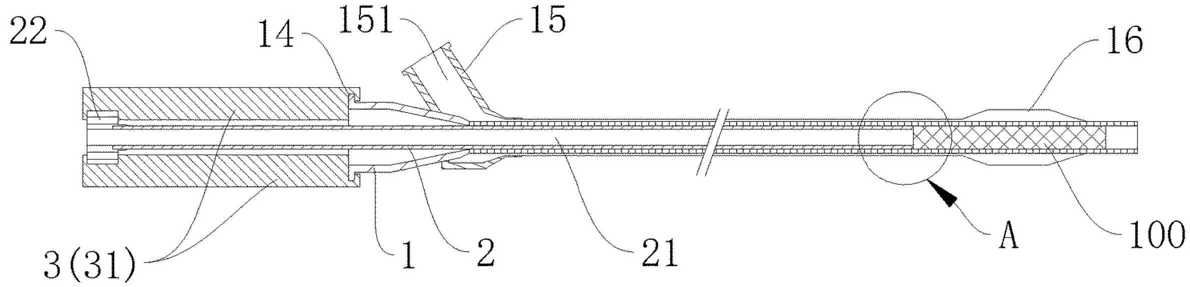
FIG. 1 is a sectional view of a balloon stent installation device according to the present application.
Figure 2:
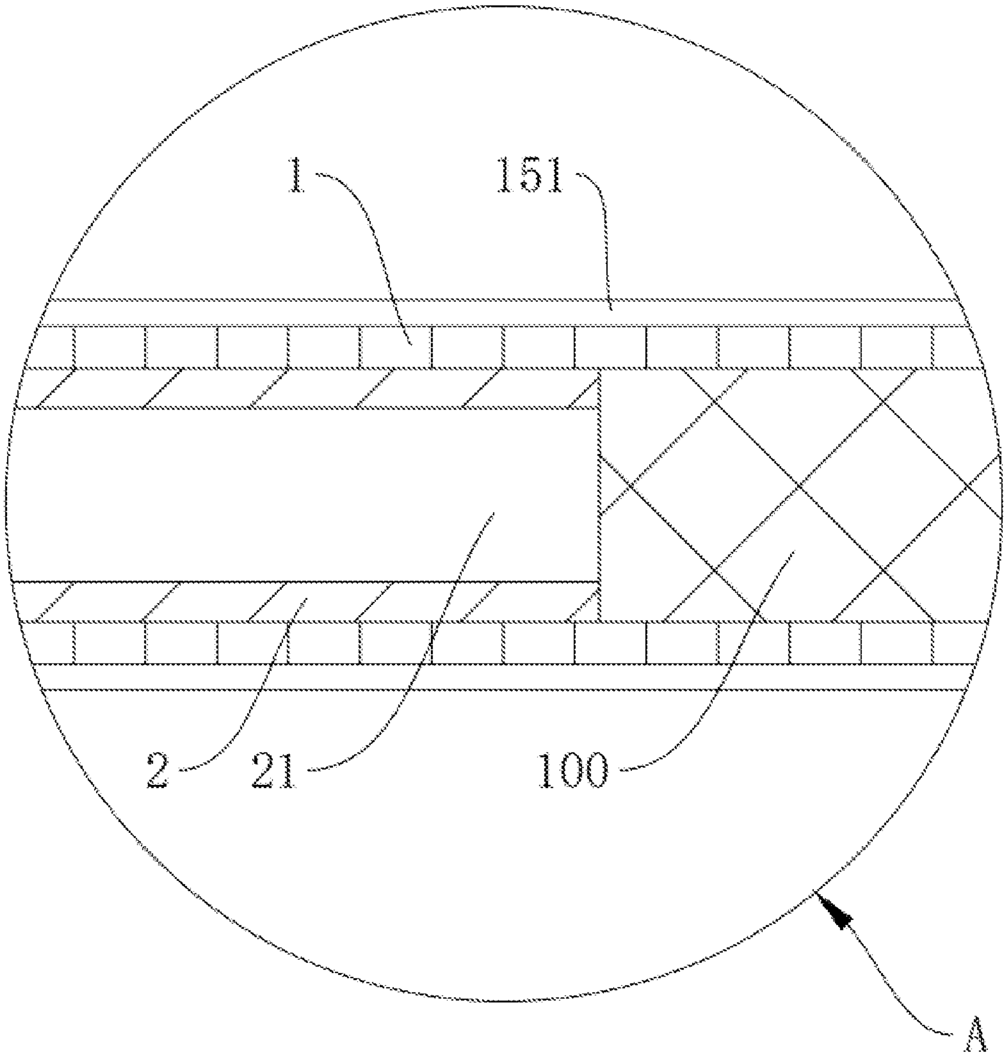
FIG. 2 is a partially enlarged view of part A of FIG. 1.
Figure 3:
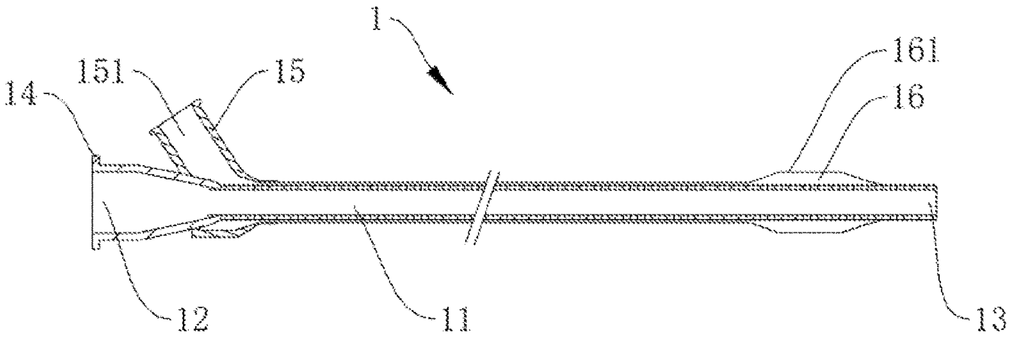
FIG. 3 is a sectional view of a balloon dilatation catheter according to the present application.

100 self-expandable stent
200 lesion site
1 balloon dilatation catheter
11 first through hole
12 inlet
13 outlet
14 first handle
15 connection port
151 fluid channel
16 expansion part
161 expansion membrane
2 stent release tube
21 second through hole
22 second handle
3 stopper assembly
31 stopper block
32 card slot
33 groove
4 micro guidewire

DETAILED DESCRIPTION

Hereinafter the present application is described in conjunction with drawings and embodiments. It is to be understood that the embodiments set forth below are merely intended to illustrate the present application. It is to be further noted that for convenience of description, only some but not all structures related to the present application are shown in the accompanying drawings.

In the description of the present application, terms “connected to each other”, “connected”, or “secured” is to be construed in a broad sense, for example, as securely connected, detachably connected integrated; mechanically connected or electrically connected; directly connected to each other or indirectly connected to each other via an intermediary; or internally connected between two elements or interaction relations between two elements. For those of ordinary skill in the art, meanings of the preceding terms in the present application can be understood according to actual situations.

In the present application, when a first feature is described as “above” or “below” a second feature, the first feature and the second feature may be in direct contact or be in contact via another feature between the two features instead of being in direct contact. Moreover, when the first feature is “on”, “above”, or “over” the second feature, the first feature is right on, above, or over the second feature, or the first feature is obliquely on, above, or over the second feature, or the first feature is simply at a higher level than the second feature. When the first feature is “under”, “below”, or “underneath” the second feature, the first feature is right under, below, or underneath the second feature, or the first feature is obliquely under, below, or underneath the second feature, or the first feature is simply at a lower level than the second feature.

In the description of the embodiments, orientations or position relations indicated by terms such as “above”, “below”, “left”, and “right” are based on the drawings. These orientations or position relations are intended only to facilitate the description and simplify an operation and not to indicate or imply that a device or element referred to must have such particular orientations or must be configured or operated in such particular orientations. In addition, terms “first” and “second” are used only to distinguish between descriptions and have no special meaning.

During the operation of a related vascular stent implantation, a surgeon needs to first deliver a microcatheter and a microguidewire to the lesion, then remove the microcatheter, insert a balloon catheter to pre-expand the lesion, then withdraw the balloon catheter, insert the microcatheter, and then, deliver the stent through the microcatheter to the lesion to release the stent and the stent is automatically stretched to dilate the blood vessel. In the preceding process, the microcatheter and the balloon catheter need to be alternately inserted into the blood vessel multiple times, which is prone to cause complications and increase operation time.

To solve the preceding problems, this embodiment provides a balloon stent installation device (for example, an integrally exchangeable balloon stent installation device), as shown in FIGS. 1 to 6. The balloon stent installation device includes a balloon dilatation catheter 1 and a stent release tube 2. The balloon stent installation device is used to install a self-expandable stent 100 to a lesion site 200 of a blood vessel.

Alternatively, as shown in FIGS. 1 to 3 and FIG. 6, the balloon dilatation catheter 1 is provided with a first through hole 11 along the length direction. An inlet 12 is disposed at a proximal end of the first through hole 11. An outlet 13 is disposed at a distal end of the first through hole 11. An expansion part 16 is disposed at a distal end of the balloon dilatation catheter 1. The self-expandable stent 100 can be slidably installed in the first through hole 11. The self-expandable stent 100 is located at the distal end of the balloon dilatation catheter 1. The stent release tube 2 penetrates the first through hole 11 through the inlet 12 and is slidably disposed in the first through hole 11 of the balloon dilatation catheter 1. A distal end of the stent release tube 2 abuts against the self-expandable stent 100. The stent release tube 2 is provided with a second through hole 21 along the length direction. The balloon dilatation catheter 1 and the stent release tube 2 are configured to enable a micro guidewire 4 to sequentially insert through the outlet 13 of the first through hole 11, the self-expandable stent 100, and the second through hole 21.

In this embodiment, in installing the stent, the compressed self-expandable stent 100 can be installed to a distal end of the balloon dilatation catheter 1, and the stent release tube 2 can be installed in the first through hole 11 through the inlet 12. The micro guidewire 4 is inserted sequentially through the outlet 13 of the first through hole 11, the self-expandable stent 100, and the second through hole 21. The balloon dilatation catheter 1 cooperates with the micro guidewire 4 to push the expansion part 16 of the balloon dilatation catheter 1 to the lesion site 200. Positive pressure is applied to the expansion part 16 to stretch out the lesion site 200. Negative pressure is applied to the expansion part 16, and the balloon dilatation catheter 1 is withdrawn. When the balloon dilatation catheter 1 is being withdrawn, the stent release tube 2 slides within the first through hole 11 relative to the balloon dilatation catheter 1 until the stent release tube 2 pushes the self-expandable stent 100 out of the first through hole 11. The self-expandable stent 100, after being detached from the first through hole 11, automatically expands to achieve blood vessel expansion. While the self-expandable stent 100 automatically expands after being detached from the first through hole 11, the balloon dilatation catheter 1 and the stent release tube 2 are withdrawn to complete the delivery and installation of the self-expandable stent 100. In this embodiment, with a balloon dilatation catheter 1 installed only once, a self-expandable stent 100 can be delivered and installed, so that a blood vessel can be dilated, operation steps can be reduced, the times of instruments exchanged in a patient’s body and operation time can be reduced, and the success rate of the operation can be improved.

Figure 4:
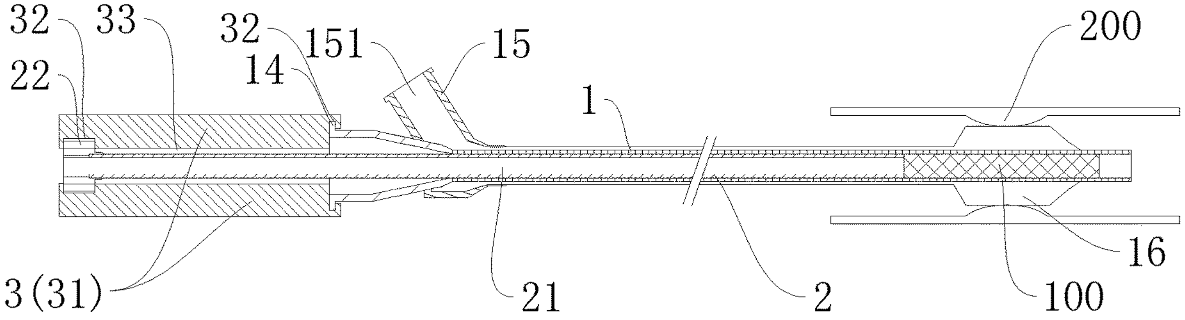
FIG. 4 is a sectional view of a self-expandable stent installation in a first state according to the present application.

Alternatively, as shown in FIGS. 1 and 4, the balloon stent installation device also includes a stopper assembly 3. A first handle 14 is disposed at a proximal end of the balloon dilatation catheter. A second handle 22 is disposed at a proximal end of the stent release tube 2. The stopper assembly 3 is provided with two card slots 32 spaced apart. A cavity is disposed between the two card slots 32. The stopper assembly 3 is detachably installed on the first handle 14 and the second handle 22 through the two card slots 32. Partial sidewall of the stent release tube 2 is located in the cavity. The distance between the two card slots 32 is no less than the length of the self-expandable stent 100. The stopper assembly 3 is installed on the first handle 14 and the second handle 22 to ensure that the balloon dilatation catheter 1 and the stent release tube 2 remain relatively stationary during entry of the balloon dilatation catheter 1 into the blood vessel, preventing the stent release tube 2 from sliding relative to the balloon dilatation catheter 1 so as to avoid pushing out of the self-expandable stent 100 in advance.

Figure 5:
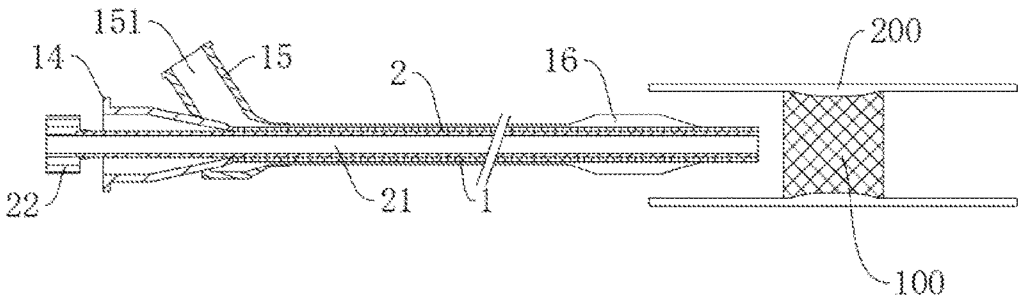
FIG. 5 is a sectional view of a self-expandable stent installation in a second state according to the present application.
Figure 6:
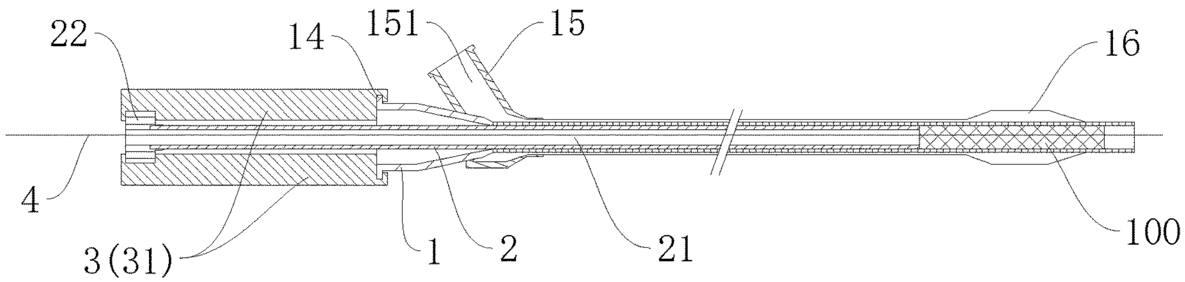
FIG. 6 is a sectional view of a balloon stent installation device according to the present application.

As shown in FIG. 5, when the expansion part 16 of the balloon dilatation catheter 1 reaches the lesion site 200, the stopper assembly 3 is disassembled, and the balloon dilatation catheter 1 is withdrawn. Since the stent release tube 2 remains stationary, the stent release tube 2 can push out the self-expandable stent 100. The distance between the two card slots 32 is no less than the length of the self-expandable stent 100. The advantages of the configuration is to prevent the relative sliding distance between the stent release tube 2 and the balloon dilatation catheter 1 from being insufficient, so that the self-expandable stent 100 can be completely pushed out.

In an embodiment, alternatively, the distance between the two card slots 32 is the same as the distance that the stent release tube 2 pushes the self-expandable stent 100. The distance between the two card slots 32 is reasonably configured so that it is ensured that at the initial stage of withdrawal of the balloon dilatation catheter 1, the balloon dilatation catheter 1 slides relative to the stent release tube 2, and the stent release tube 2 remains stationary until the first handle 14 and the second handle 22 are in contact, and the balloon dilatation catheter 1 and the stent release tube 2 are withdrawn simultaneously, thereby providing a preset distance for the push-out distance of the stent release tube 2. In this manner, the withdrawal efficiency of the balloon stent installation device is improved.

Alternatively, the stopper assembly 3 includes two stopper blocks 31 that can be spliced. The sidewall of each of the two stopper blocks 31 is respectively provided with a groove 33, the groove 33 on one of the two stopper blocks 31 is opposite to the groove 33 on another of the two stopper blocks 31. After the two stopper blocks 31 are spliced, the opposite grooves 33 are spliced to form the two card slots 32 and the cavity. The two stopper blocks 31 are assembled in a spliced manner. The first handle 14 and the second handle 22 provide positioning for the assembly of the two stopper blocks 31. The stopper assembly 3 is good in simple operation, easy disassembly and assembly, and strong practicability.

In an embodiment, alternatively, the sidewall of the balloon dilatation catheter 1 includes an inner wall and an outer wall, a fluid channel 151 is disposed between the inner wall and the outer wall. The expansion part 16 is an expansion membrane 161 connected to the outer wall. A proximal end of the fluid channel 151 is connected to a fluid source. A distal end of the fluid channel 151 communicates with the expansion membrane 161. When the fluid source releases fluid, the fluid in the expansion membrane 161 increases to generate positive pressure, and the expansion membrane 161 expands outwardly to stretch out the lesion site 200. When the fluid source recovers the fluid, the fluid in the expansion membrane 161 decreases to generate negative pressure, and the expansion membrane 161 retracts to facilitate the withdrawal of the balloon dilatation catheter 1. In this embodiment, the fluid released by the fluid source is a liquid. Of course, in other embodiments, fluid may also be a gas. Alternatively, a connection port 15 is disposed on the outer wall close to a proximal end of the balloon dilatation catheter 1. The connection port 15 is configured to connect the fluid source to facilitate the connection of the fluid source.

In an embodiment, alternatively, to facilitate an operator to obtain the position of the distal end of the balloon dilatation catheter 1 and the position of the self-expandable stent 100 in the blood vessel, a developing ring or a developing winding is installed at the distal end of the balloon dilatation catheter 1 and a developing ring or a developing winding is also installed on the outside of the self-expandable stent 100. Under radiation, the position of the distal end of the balloon dilatation catheter 1 can be obtained via an instrument, and the position and state of the self-expandable stent 100 can be detected via the instrument. The developing ring may be fixed by bonding. The developing winding may be fixed by winding.

Figure 7:
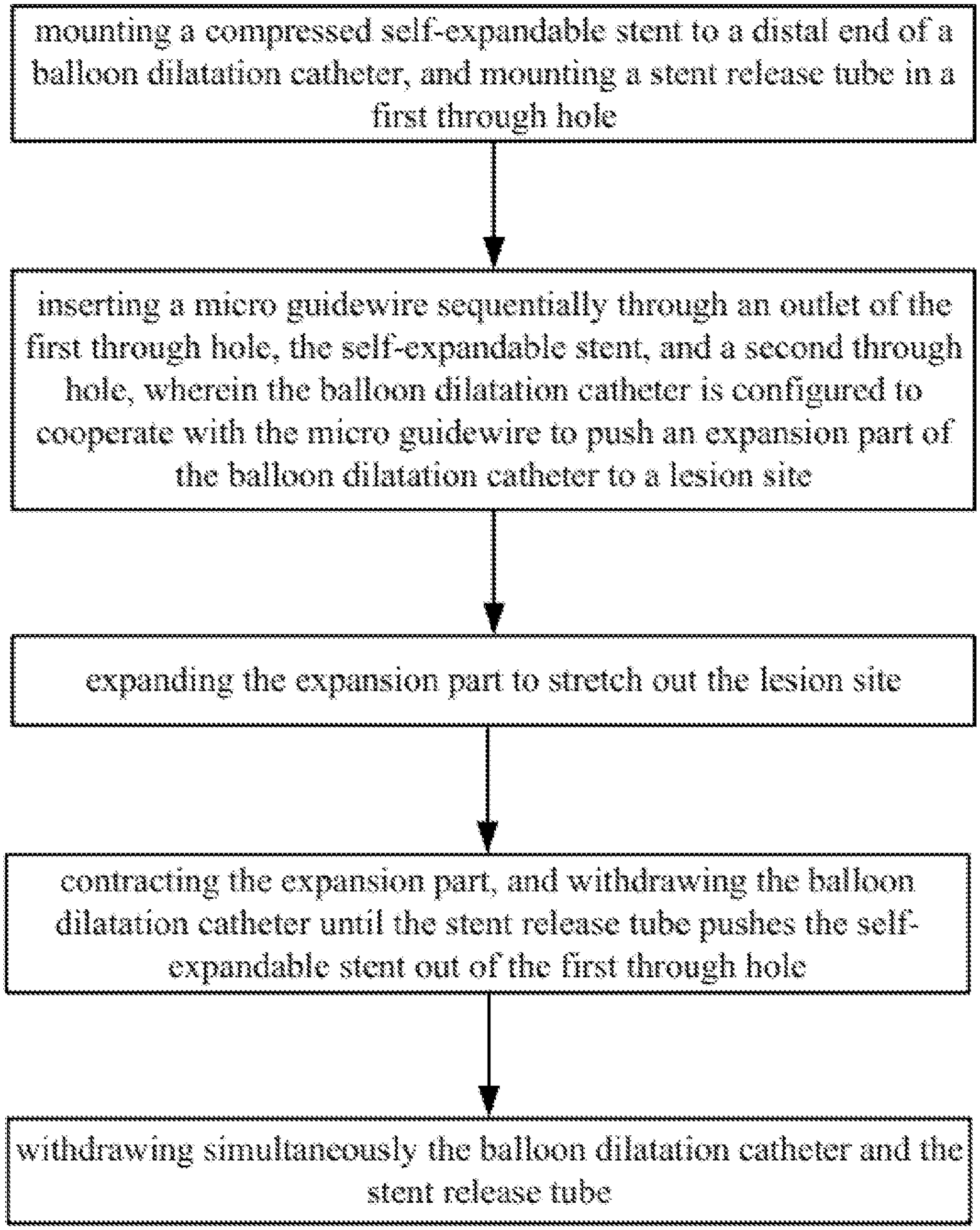
FIG. 7 is a flow chart of a stent installation method using the balloon stent installation device according to the present application.

This embodiment also provides a stent installation method that uses the balloon stent installation device described above. As shown in FIG. 7, the method includes the steps described below.

Step 1: A compressed self-expandable stent 100 is mounted to a distal end of a balloon dilatation catheter 1, and a stent release tube 2 is mounted in a first through hole 11.

Step 2: A micro guidewire 4 is inserted sequentially through an outlet 13 of the first through hole 11, the self-expandable stent 100, and a second through hole 21. The balloon dilatation catheter 1 cooperates with the micro guidewire 4 to push an expansion part 16 of the balloon dilatation catheter 1 to a lesion site 200.

Step 3: The expansion part 16 expands to stretch out the lesion site 200.

Step 4: After the expansion part 16 contracts, the balloon dilatation catheter 1 is withdrawn until the stent release tube 2 pushes the self-expandable stent 100 out of the first through hole 11, and the self-expandable stent 100 automatically expands to stretch out the lesion site 200.

Step 5: The balloon dilatation catheter 1 and the stent release tube 2 are withdrawn simultaneously to complete the installation operation of the self-expandable stent 100.

Alternatively, when the stopper assembly 3 is used, in step 2, the stopper assembly 3 is mounted on the first handle 14 and the second handle 22 after the stent release tube 2 is mounted in the first through hole 11 to improve the stability of the delivery of the balloon dilatation catheter 1. In step 4, after the expansion part 16 is retracted, the stopper assembly 3 is removed.

In this embodiment, in installing the stent, a compressed self-expandable stent is mounted to the distal end of a balloon dilatation catheter. The stent release tube is mounted in a first through hole through an inlet. A micro guidewire 4 is inserted sequentially through an outlet of the first through hole, the self-expandable stent, and the second through hole. The balloon dilatation catheter cooperates with the micro guidewire 4 to push the expansion part of the balloon dilatation catheter to the lesion site. Positive pressure is applied to the expansion part to stretch out the lesion site. Negative pressure is applied to the expansion part, and the balloon dilatation catheter is withdrawn. When withdrawing the balloon dilatation catheter 1, the stent release tube slides within the first through hole relative to the balloon dilatation catheter until the stent release tube pushes the self-expandable stent out of the first through hole. The self-expandable stent, after being detached from the first through hole, automatically expands to achieve blood vessel stretch out. While the self-expandable stent 100 automatically expands after being detached from the first through hole 11, the balloon dilatation catheter and the stent release tube are withdrawn to complete the delivery and installation of the self-expandable stent. In this embodiment of the present application, with a balloon dilatation catheter mounted only once, the self-expandable stent can be delivered and mounted, so that the blood vessel is dilated, operation steps are reduced, the times of instruments exchanged in a patient's body and operation time can be reduced, and the success rate of the operation can be improved.

What is claimed is:

1. A balloon stent installation device, which is configured to install a self-expandable stent to a lesion site of a blood vessel, wherein the balloon stent installation device comprises:

a balloon dilatation catheter provided with a first through hole in a length direction, wherein an inlet is disposed at a proximal end of the first through hole, and an outlet is disposed at a distal end of the first through hole, and wherein an expansion part is disposed at a distal end of the balloon dilatation catheter, the self-expandable stent is slidably mounted in the first through hole, and the self-expandable stent is located at the distal end of the balloon dilatation catheter;

a stent release tube, wherein the stent release tube is configured to penetrate the first through hole through the inlet and is slidably disposed in the first through hole of the balloon dilatation catheter, and a distal end of the stent release tube abuts against the self-expandable stent and wherein the stent release tube is provided with a second through hole along the length direction, and the balloon dilatation catheter and the stent release tube are configured to enable a micro guidewire to be inserted sequentially through the outlet of the first through hole, the self-expandable stent, and the second through hole; and a stopper assembly, wherein a first handle is disposed at a proximal end of the balloon dilatation catheter, a second handle is disposed at a proximal end of the stent release tube, and the stopper assembly is provided with two card slots spaced apart, wherein a cavity is disposed between the two card slots, the stopper assembly is detachably mounted on the first handle and the second handle through the two card slots, a partial sidewall of the stent release tube is located in the cavity, wherein the stopper assembly comprises two stopper blocks that can be spliced, a sidewall of each of the two stopper blocks is respectively provided with a groove, the groove on one of the two stopper blocks is opposite to the groove on another of the two stopper blocks, and in a situation where the two stopper blocks are spliced, the opposite grooves are configured to be spliced to form the two card slots and the cavity; and wherein the distance between the two card slots is the same as a distance that the stent release tube pushes the self-expandable stent.

2. The balloon stent installation device of claim 1, wherein a sidewall of the balloon dilatation catheter comprises an inner wall and an outer wall, a fluid channel is disposed between the inner wall and the outer wall, the expansion part is an expansion membrane connected to the outer wall, a proximal end of the fluid channel is connected to a fluid source, a distal end of the fluid channel is configured to communicate with the expansion membrane, and the fluid source is configured to control contraction and expansion of the expansion membrane.

3. The balloon stent installation device of claim 2, wherein a connection port is disposed on the outer wall close to a proximal end of the balloon dilatation catheter, and the connection port is configured to connect to the fluid source.

4. The balloon stent installation device of claim 2, wherein fluid released by the fluid source is a liquid.

5. The balloon stent installation device of claim 1, wherein a developing ring or a developing winding is mounted on an outside of the self-expandable stent.

6. The balloon stent installation device of claim 2, wherein a developing ring or a developing winding is mounted at the distal end of the balloon dilatation catheter.

7. A stent installation method using the balloon stent installation device of claim 1, comprising the following steps:

mounting the self-expandable stent compressed to the distal end of the balloon dilatation catheter, and mounting the stent release tube in the first through hole;

inserting the micro guidewire sequentially through the outlet of the first through hole, the self-expandable stent, and the second through hole, wherein the balloon dilatation catheter is configured to cooperate with the micro guidewire to push the expansion part of the balloon dilatation catheter to the lesion site;

expanding the expansion part to stretch out the lesion site;

contracting the expansion part, and withdrawing the balloon dilatation catheter until the stent release tube pushes the self-expandable stent out of the first through hole; and withdrawing simultaneously the balloon dilatation catheter and the stent release tube.

* * * * *